United States Patent [19]

Midorikawa

[11] Patent Number: 5,623,934
[45] Date of Patent: Apr. 29, 1997

[54] INTERFERENCE-DETECTING MEDICAL MONITORING APPARATUS AND METHOD

[75] Inventor: Yoshikazu Midorikawa, Tokyo, Japan

[73] Assignee: Nihon Kohden Corporation, Tokyo, Japan

[21] Appl. No.: 496,693

[22] Filed: Jun. 29, 1995

[30] Foreign Application Priority Data

Jun. 30, 1994 [JP] Japan ................................. 6-149370

[51] Int. Cl.⁶ ............................................. A61N 5/04
[52] U.S. Cl. ...................................... 128/696; 128/903
[58] Field of Search ........................... 128/696, 903

[56] References Cited

U.S. PATENT DOCUMENTS

| | | | |
|---|---|---|---|
| 3,953,848 | 4/1976 | Dillman et al. | 128/903 |
| 3,972,320 | 8/1976 | Kolman | 128/903 |
| 4,550,370 | 10/1985 | Baker | 128/696 |
| 4,979,506 | 12/1990 | Silvian | 128/903 |
| 5,168,871 | 12/1992 | Grevious | 128/903 |

*Primary Examiner*—William E. Kamm
*Attorney, Agent, or Firm*—Sughrue, Mion, zinn, Macpeak & Seas

[57] ABSTRACT

There is disclosed a medical monitoring apparatus for remotely monitoring a subject by receiving a signal containing remotely monitoring data, which consists of living body data and channel IDs, from a transmitter for the subject in a digital wireless manner. The medical monitoring apparatus comprises: a channel ID check section for determining whether or not the received remote monitoring data contains the same channel ID as that stored in advance in the receiver; a receiving level check section for checking whether or not an intensity of the receiving signal is high enough to be in a receivable level; an interference state check section for checking whether or not a radio interference state is present, on the basis of the output signal of the channel ID check section and the receiving level check section; and display means for displaying a radio interference state on the basis of the output signal of the interference state check section.

3 Claims, 2 Drawing Sheets

INTERFERENCE-DETECTING MEDICAL MONITORING APPARATUS AND METHOD

BACKGROUND OF THE INVENTION

1. Field of the Invention

The present invention relates to a medical monitoring apparatus used for remotely monitoring an electrocardiogram and respiration of a subject by a digital telemeter. More particularly, the invention relates to a medical monitoring apparatus capable of automatically checking an interference.

2. Related Art

There is known a medical monitoring apparatus used for remotely monitoring an electrocardiogram and respiration of a subject. Depending on the form of the signal processed, the medical monitoring apparatus is categorized as being either of the analog type or of the digital type. To check its receiving condition, the analog medical monitoring apparatus uses an intensity of an electric field of the receiving signal, while the digital medical monitoring apparatus detects presence or absence of a channel ID.

In the communication between the transmitter and the medical monitoring apparatus, there is a case where an intensity of an electric field of a signal received from the transmitter is excessively decreased. This is caused, for example, when something is wrong with the transmitter, a battery is flat, a distance between the transmitter and the medical monitoring apparatus is too long. In this case, the analog medical monitoring apparatus displays a message of no reception. The medical monitoring apparatus is frequently used, together with other medical apparatuses. These other medical apparatuses, when operating, emit radio waves. The analog medical monitoring apparatus is sensitive to these interference radio waves leaking from the other medical apparatuses. When any of the interference radio waves is more intensive than the radio wave received from the transmitter, the medical monitoring apparatus mistakenly recognizes the interference radio wave as its intended radio wave and displays it as the intended data signal. This phenomenon is called a radio interference.

The digital medical monitoring apparatus also displays "no reception" when it cannot discriminate a channel ID for the reason that something is wrong with the transmitting system including the transmitter or the receiving system including the medical monitoring apparatus. No reception is displayed also when the medical monitoring apparatus fails to discriminate a channel ID by the interference.

Thus, when interference occurs, the analog medical monitoring apparatus displays the waveform of the interference radio wave from another medical apparatus, and the digital medical monitoring apparatus displays no reception. In other words, neither of the conventional medical monitoring apparatuses can distinctly show the interference.

As described above, when the radio wave leaking from another medical device, used near the medical monitoring apparatus, has a frequency equal to that of a radio wave used in the medical monitoring apparatus, interference occurs. In this case, the conventional medical monitoring apparatus can indistinctly show the interference. In other words, any of the conventional medical monitoring apparatuses cannot clearly show the cause of an erroneous signal in the medical monitoring apparatus, i.e., the failure in the transmitting system and/or the receiving system or interference.

SUMMARY OF THE INVENTION

The present invention has been made in view of the above circumstances and has an object to provide a medical monitoring apparatus which can distinctly and easily show interference.

To achieve the above object, the present invention provides a medical monitoring apparatus for remotely monitoring a subject by receiving a signal containing remotely monitoring data, which consists of living body data and channel IDs, from a transmitter for the subject in a digital wireless manner.

The medical monitoring apparatus comprises: a channel ID check section for determining whether or not the received remote monitoring data contains the same channel ID as that stored in advance in the receiver; a receiving level check section for checking whether or not an intensity of the receiving signal is high enough to be in a receivable level; an interference state check section for checking whether or not an interference state is present, on the basis of the output signal of the channel ID check section and the receiving level check section; and display means for displaying an interference state on the basis of the output signal of the interference state check section.

When the channel ID check section determines that the receiving data does not contain the intended channel ID, and the receiving level check section determines that the intensity of an electric field of the receiving signal is in a receivable level, the interference check section determines that the medical monitoring apparatus is in an interference state. This interference state is displayed by the display means.

DETAILED DESCRIPTION OF THE PREFERRED EMBODIMENTS

The preferred embodiment of the present invention will be described with reference to the accompanying drawings.

Figure 1:
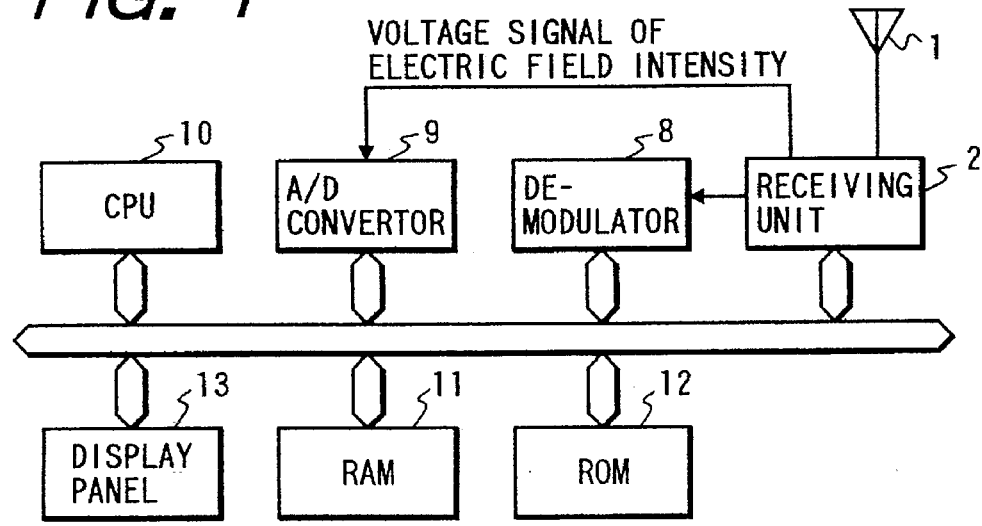
FIG. 1 is a block diagram showing an embodiment of a medial monitoring apparatus according to the present invention.

An embodiment of a medical monitoring apparatus according to the present invention is shown in block form in FIG. 1. The medical monitoring apparatus serves as a part of a digital telemeter system.

In the figure, remote monitoring data contained in a living body signal carried by a high frequency FM signal of the frequency band of 400 MHz, for example, is received by an antenna 1 of the medical monitoring apparatus. The received data signal enters a receiving unit 2.

Figure 2:
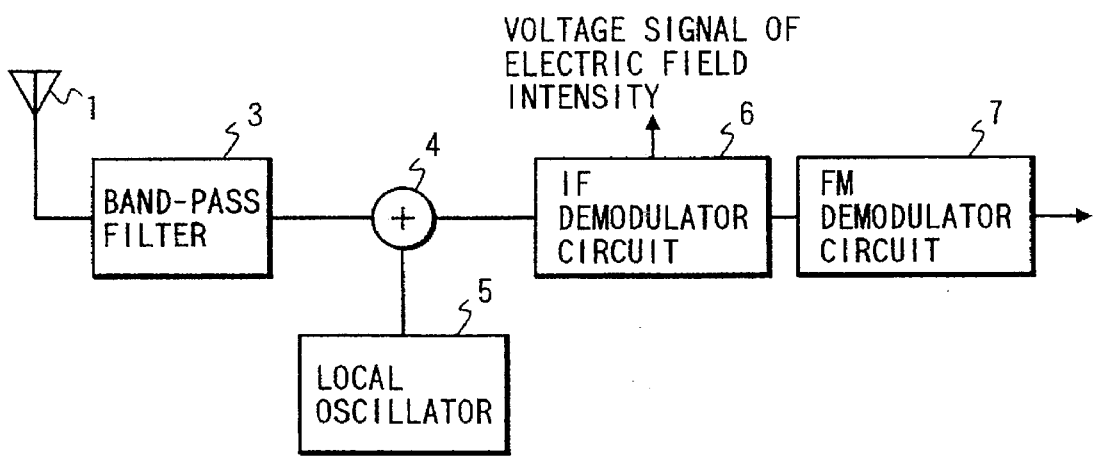
FIG. 2 is a block diagram showing a receiver unit of the medial monitoring apparatus of FIG. 1.

The receiving unit 2, as shown in FIG. 2, is made up of a band-pass filter 3, a local oscillator 5, a mixer 4, an intermediate frequency demodulator circuit 6, and an FM demodulator circuit 7. The band-pass filter 3 allows the received signals of specific frequencies to selectively pass therethrough. The local oscillator 5 oscillates or generates a local frequency signal.

In the receiving unit 2, the frequency of the signal generated by the local oscillator 5 is adjusted so as to be equal to the frequency of a receiving signal. To register the frequency of the receiving signal, a channel ID (a channel number set in the medical monitoring apparatus) is stored into a RAM 11.

Figure 3:
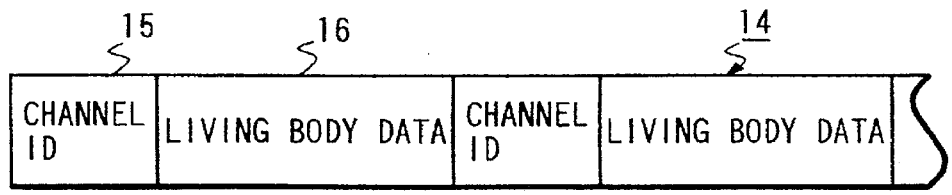
FIG. 3 is a diagram showing the remote monitoring data handled in the apparatus.

FIG. 3 is a diagram showing a format of remote monitoring data 14, which comes from a transmitter. As shown, the remote monitoring data 14 includes a channel ID (identity) 15 and living body data 16 containing, for example, electrocardiogram data and respiration data.

An output signal of the receiving unit 2 is demodulated by a demodulator circuit 8, and input into a CPU 10 where the data contained in the signal is properly processed. The processed data signal containing electrocardiogram data and respiration data, for example, is visually presented by a display panel 13.

The IF demodulator circuit 6 of the receiving unit 2 produces a voltage signal representative of an intensity of an electric field. The voltage signal is converted into a digital signal by an A/D convertor 9. The thus digitized signal is input into the CPU 10 where it is properly processed.

A ROM 12 stores programs to be executed by the CPU 10.

The CPU 10 has multiple of check functions, for example, a channel ID check, a receiving level check, and an interference check.

Figure 4:
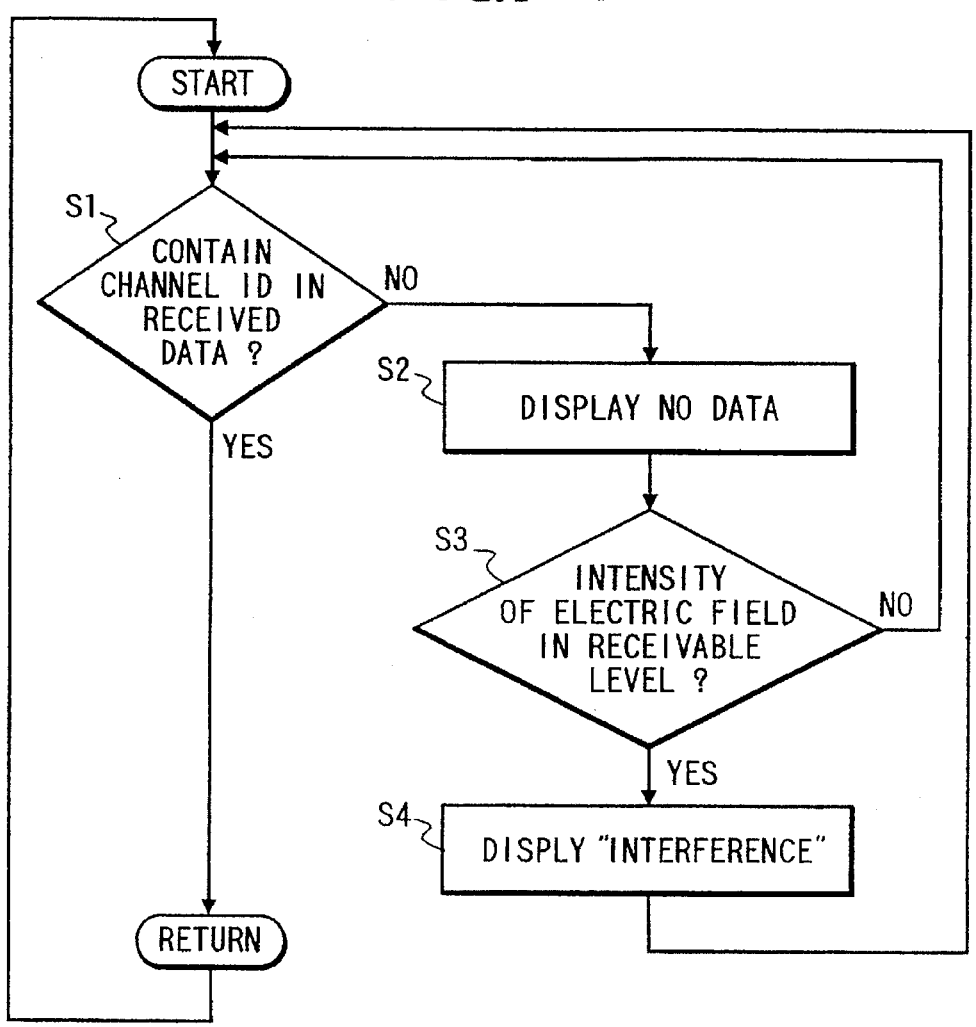
FIG. 4 is a flowchart showing the operation of checking a radio interference in the medial monitoring apparatus.

A process of checking an interference state in the medical monitoring apparatus will be described with reference to a flowchart shown in FIG. 4.

The CPU 10 checks, in a step S1, if the received data contains a channel ID, which is the same as a channel ID stored in the RAM 11. If it contains such a channel ID, it is judged that the medical monitoring apparatus normally receives the remote monitoring data. Accordingly, the interference state check process is placed into a stand-by mode.

If the received data does not contain such a channel ID, the CPU 10 in a step S2 displays a message that no data is received, by the display panel 13.

Figure 5:
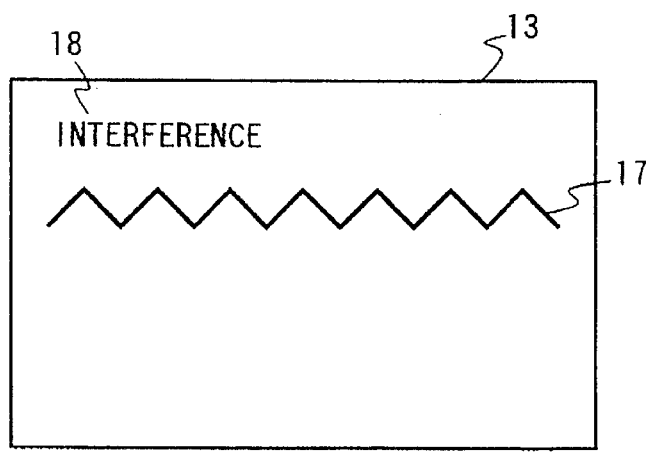
FIG. 5 is a diagram showing an example of interference display on the display panel.

This message is displayed in the form of a triangle waveform in an example of FIG. 5.

In a step S3, the CPU 10 checks if an intensity of an electric field of the receiving signal is high enough to be at a receivable level, on the basis of the data from the A/D convertor 9. If the receiving level is insufficiently high, the CPU 10 returns to the step S1.

If it is sufficiently high, the CPU 10 determines that interference has occurred and displays the interference by the display panel 13 in a step S4.

In this instance of the embodiment, the interference state is displayed in the form of a word "Interference" on the display panel.

As described above, when the intensity of the electric field of the receiving signal is at a receivable level and the channel ID is not found in the receiving data, the medical monitoring apparatus judges that interference has occurred preventing acceptable signal reception. Thus, the check as to whether or not interference is present can easily be made.

As seen from the foregoing description, the medical monitoring apparatus of the present invention can distinctly show that the medical monitoring apparatus in an interference state in an easy manner.

Accordingly, the invention succeeds in eliminating troublesome check work of whether the power source of the transmitter for a patient is turned off for checking the radio interference.

It should be understood by those skilled in the art that the foregoing description is a preferred embodiment of the disclosed apparatus and that various changes and modifications may be made in the invention without departing from the spirit and scope thereof.

What is claimed is:

1. A medical monitoring apparatus comprising:
   a receiver for receiving an input signal;
   channel ID check means, coupled to said receiver, for determining whether remote monitoring data in said input signal received by said receiver contains a channel ID which is the same as a channel ID stored in advance in said receiver;
   receiving level check means for checking whether an intensity of said input signal is higher than a predetermined receivable level;
   interference state check means for checking whether radio interference has effected said input signal based upon an output signal of said channel ID check means and an output signal of said receiving level check means; and
   display means for displaying a radio interference state based upon an output signal of said interference state check means.

2. The medical monitoring apparatus as claimed in claim 1, wherein said receiver detects living body data and channel ID data in said remote monitoring data.

3. A method for checking a medical monitoring apparatus comprising the steps of:
   receiving an input signal at a receiver;
   determining whether remote monitoring data included in said input signal contains a channel ID which is the same as a channel ID stored in advance in said receiver;
   checking whether an intensity of said input signal is higher than a predetermined receivable level; and
   checking whether radio interference has effected said input signal based upon a result of said determining step and said step of checking said intensity of said input signal.

* * * * *